US012805756B2

(12) United States Patent
Oumnia

(10) Patent No.: US 12,805,756 B2
(45) Date of Patent: Nov. 24, 2026

(54) METHOD AND SYSTEM FOR DETERMINING A VALUE OF AN ADVANCED BIOMECHANICAL GAIT PARAMETER

(71) Applicants: ZHOR TECH, Nancy (FR); DIGITSOLE, Nancy (FR)

(72) Inventor: Karim Oumnia, Nancy (FR)

( * ) Notice: Subject to any disclaimer, the term of this patent is extended or adjusted under 35 U.S.C. 154(b) by 1372 days.

(21) Appl. No.: 17/605,815

(22) PCT Filed: Apr. 25, 2020

(86) PCT No.: PCT/FR2020/050714
§ 371 (c)(1),
(2) Date: Mar. 24, 2022

(87) PCT Pub. No.: WO2020/217037
PCT Pub. Date: Oct. 29, 2020

(65) Prior Publication Data

US 2022/0240814 A1 Aug. 4, 2022

(30) Foreign Application Priority Data

Apr. 25, 2019 (FR) ...................................... 1904412

(51) Int. Cl.
*A61B 5/11* (2006.01)
*A61B 5/00* (2006.01)
(Continued)

(52) U.S. Cl.
CPC ............ *A61B 5/112* (2013.01); *A61B 5/6829* (2013.01); *A61B 5/7282* (2013.01); *G16H 20/30* (2018.01);
(Continued)

(58) Field of Classification Search
CPC ..... A61B 5/112; A61B 5/6829; A61B 5/7282; A61B 2562/0219; A61B 2560/0214;
(Continued)

(56) References Cited

U.S. PATENT DOCUMENTS 8,628,485 B2 * 1/2014 Wilson ................. A61B 5/6807 600/595
9,232,911 B2 * 1/2016 Wilson ................. A61B 5/6807
(Continued)

FOREIGN PATENT DOCUMENTS

CN 105631195 A 6/2016
EP 1998849 B1 * 12/2014 ........... A61B 5/0022
(Continued)

OTHER PUBLICATIONS

Rampp, et al. “Inertial Sensor-Based Stride Parameter Calculation From Gait Sequences in Geriatric Patients.” Apr. 1, 2015 (Apr. 1, 2015). IEEE Transactions in Biomedical Engineering. vol. 62, No. 4, p. 1089-1097.

(Continued)

*Primary Examiner* — Peter J Macchiarolo
(74) *Attorney, Agent, or Firm* — Tucker Ellis LLP

(57) ABSTRACT

The invention relates to a method for determining an advanced biomechanical gait parameter value from data generated by one or more motion sensors of a sole, said method including: a step (200) of acquiring data generated by one or more motion sensors of a sole; a step (300) of calculating an orientation value of the sole; a step (600) of identifying an activity associated with a motion unit; a step (700) of identifying at least two key moments of the motion unit for which an activity has been identified; and a step (800) of determining an advanced biomechanical gait parameter value, said determination including calculating a biomechanical gait parameter value for at least one of the identified key moments and from the acceleration, angular velocity, and/or orientation values of the sole.

15 Claims, 4 Drawing Sheets

(51) Int. Cl.
*G16H 20/30* (2018.01)
*G16H 40/63* (2018.01)

(52) U.S. Cl.
CPC ...... *G16H 40/63* (2018.01); *A61B 2562/0219* (2013.01)

(58) Field of Classification Search
CPC .... A61B 5/1121; A61B 5/6807; G16H 20/30; G16H 40/63; G16H 40/67; G16H 50/20
See application file for complete search history.

(56) References Cited

U.S. PATENT DOCUMENTS

| | | | | |
|---|---|---|---|---|
| 2008/0214360 | A1* | 9/2008 | Stirling | A61B 5/6807 482/9 |
| 2011/0022349 | A1* | 1/2011 | Stirling | A61B 5/1038 702/141 |
| 2012/0035509 | A1* | 2/2012 | Wilson | A61B 5/1038 600/592 |
| 2014/0094717 | A1* | 4/2014 | Wilson | A61B 5/112 600/592 |
| 2016/0180440 | A1* | 6/2016 | Dibenedetto | G06Q 30/02 705/26.7 |
| 2017/0273601 | A1* | 9/2017 | Wang | A61B 5/1118 |
| 2018/0263532 | A1* | 9/2018 | Smulyan | A61B 5/0002 |
| 2019/0150793 | A1* | 5/2019 | Barth | A61B 5/112 |
| 2020/0318972 | A1* | 10/2020 | Couvet | G07C 9/28 |
| 2025/0235113 | A1* | 7/2025 | Poltorak | A61B 5/0022 |

FOREIGN PATENT DOCUMENTS

| | | | | |
|---|---|---|---|---|
| EP | 3038042 | A1 | 6/2016 | |
| EP | 3257437 | A1 * | 12/2017 | A61B 5/6807 |
| JP | 2016032611 | * | 3/2016 | |

OTHER PUBLICATIONS

International Search Report (with translation) in PCT/FR2020/050714 dated Jun. 30, 2020, 7 pages.

Translation of Written Opinion in PCT/FR2020/050714 dated Jun. 30, 2020, 7 pages.

* cited by examiner

METHOD AND SYSTEM FOR DETERMINING A VALUE OF AN ADVANCED BIOMECHANICAL GAIT PARAMETER

The invention relates to the field of characterization of the gait, and more particularly to the determination of biomechanical gait parameter values, which may find an application in the monitoring of daily or sports activities, or the monitoring of the physiological condition of the subject under study. The invention relates to a method for determining an advanced biomechanical gait parameter value from data generated by one or more motion sensors of a sole. The invention further relates to a system for determining an advanced biomechanical gait parameter value that can implement such a method.

PRIOR ART

Human gait is a complex and cyclical process, primarily aimed at supporting the upright position and maintaining balance under static and dynamic conditions, and requiring for this the synergy of the muscles, bones, and nervous system.

Many systems have been developed over the years to study human gait. These systems involve, for example, the use of shoes equipped with pressure sensors or inertial sensors positioned in the sole, on the shoe, or at the ankle. In particular, several teams have focused on the use and processing of inertial sensor data for the analysis of human motion. These systems, based on one or more sensors, currently provide values of conventional "walking" parameters indicating, for example, information on the number of steps thanks to calculations most often carried out entirely on external terminals.

Human walking can reflect the state of certain sensory, neural, and biomechanical systems involved in gait. Thus, other teams have sought to study advanced biomechanical gait parameters such as those depending on the spatial relationship of the two feet, for example the length and width of the step. Measuring such biomechanical gait parameters usually requires specialized equipment such as video motion capture systems, thus limiting measurements to the laboratory. Technological advances in miniature inertial measurement units (accelerometers and gyroscopes) provide the opportunity to measure progress outside the laboratory. However, evaluating advanced biomechanical gait parameters from such sensors generally results in standard deviations that are too high to be properly used. They then require the implementation of numerous drift corrections in the processing algorithms.

For example, the analysis of advanced biomechanical gait parameters has been applied in the context of aging, risk of falling, spinal cord injury, diabetic neuropathy, and neurological conditions (Rebula et al. *Gait Posture.* 2013 September; 38(4): 974-980). This study showed that the use of acceleration- and angular velocity-type motion data required the implementation of corrections based on assumptions of linearity of the error and then inducing approximations on the values of the calculated parameters.

Foot elevation during the stride phase is an important indicator of the quality and safety of walking in disabled subjects. In a study dedicated to the investigation of this parameter, an average error of about 4.1 centimeters (cm) was obtained (Mariani et al. IEEE Trans. Bio-Med. Eng. 2012; 59:3162-3168). While in another study, according to the authors, the observation of performance degradation was mainly due to the flatfoot phase detection algorithm, which had some limitations when the gait was not very natural, especially in the case of a gait related to an individual having to cross obstacles (Benoussaad et al. Sensors (Basel). 2015 Dec. 23; 16(1). pii: E12). Thus, current systems for determining biomechanical gait parameter values are not satisfactory since the latter do not allow for accurate calculation of such parameters.

Technical Problem

The invention aims to overcome the disadvantages of the prior art. In particular, the invention aims to provide a method for determining an advanced biomechanical gait parameter value and capable of generating advanced biomechanical gait parameter values with lower variability. In addition, the absence of a strong need for computing resources for the steps of the method makes it possible to implement it in real time.

The invention further aims to provide a system for determining an advanced biomechanical gait parameter value, said system being capable of generating advanced biomechanical gait parameter values with lower variability.

BRIEF DESCRIPTION OF THE INVENTION

To this end, the invention relates to a method for determining an advanced biomechanical gait parameter value from data generated by one or more motion sensors of a sole, said method, performed by one or more analysis modules, including:

- A step of acquiring data generated by one or more motion sensors of a sole, said data including acceleration, angular velocity, and/or magnetic field values;
- A step of calculating an orientation value of the sole, said orientation value of the sole being calculated with respect to a terrestrial reference frame from data including the acceleration, angular velocity, and/or magnetic field values;
- A step of identifying an activity associated with a motion unit, said identification of an activity including comparing activity reference values with values selected from: acceleration, angular velocity, and/or orientation values of the sole, or global descriptive parameter values calculated from the acceleration, angular velocity, and/or orientation values of the sole;
- A step of identifying at least two key moments of the motion unit for which an activity has been identified, said step of identifying key moments including comparing motion parameter values to at least one predetermined threshold, said predetermined threshold being associated with the identified activity and said motion parameter values including the acceleration, angular velocity, and/or orientation values of the sole; and
- A step of determining an advanced biomechanical gait parameter value, said determination including calculating a biomechanical gait parameter value for at least one of the identified key moments and from the acceleration, angular velocity, and/or orientation values of the sole.

Such a method differs in particular from the existing one by the presence of an identification of an activity associated with a motion unit, on the one hand, and a determination of a biomechanical gait parameter value for at least one identified key moment, on the other hand. While conventional systems seek to identify gait parameters often from a possibly preprocessed sequence, a method according to the invention is based on a first identification of an activity and then on the determination of parameter values only on the motion units having been associated with an activity and on the basis of thresholds adapted to said activity. Thus, the accuracy of the calculation is improved, and the variability of the results is reduced. A method according to the invention then makes it possible to reliably monitor a user's gait. In addition, certain biomechanical parameters will only make sense if they are associated with a key moment in a cycle. However, thanks to these steps, the method makes it possible for the first time to obtain accurate biomechanical parameter values associated with specific moments, which then become advanced biomechanical parameters. Contrary to the literature where the parameters are calculated for all times, here the calculation is done preferably for a particular identified time.

According to other optional features of the method:

- the biomechanical gait parameter is selected from: propulsion speed, fatigue rate, Fick angle, propulsion direction, and deceleration direction. Such parameters have never been proposed in the context of gait characterization with inertial motion sensors such as in the method according to the invention. Such parameters, which can be accessed using the method according to the invention, would open up new ways of characterizing the gait.
- key moments include: heel touching the ground, toes touching the ground, heel lifting off the ground, and/or toes lifting off the ground. These key moments are the most informative.
- it further includes a step of preprocessing the acceleration, angular velocity, and orientation values of the sole, said preprocessing step including at least one processing selected from: frequency filtering, suppression of gravity on the acceleration values, suppression of gravity, suppression of noise and/or drift on the acceleration, angular velocity, and orientation values of the sole.
- the preprocessing step is carried out in an electronic box integrated into the sole. This preprocessing step can be carried out in an external electronic device such as a mobile phone or a computer server. Nevertheless, the preprocessing step is preferably carried out in an electronic box integrated into the sole. That is to say that the electronic box is preferably in the sole and not attached to an ankle or fixed to the top of a shoe. This increases the accuracy of the method.
- It further includes a step of identifying a motion unit. Such a step can be implemented by the various methods known to the one skilled in the art.
- the step of identifying an activity associated with a motion unit includes calculating one or more global descriptive parameters from the acceleration, angular velocity, and/or magnetic field values, said global descriptive parameters including a kurtosis or skewness coefficient value. Preferably, the global descriptive parameters are calculated from the acceleration and angular velocity values. Such global descriptive parameters make it possible to discriminate more effectively between activities.
- the step of identifying an activity associated with a motion unit includes calculating one or more global descriptive parameters from the acceleration, angular velocity, and/or magnetic field values, said global descriptive parameters including one or more values of similarity coefficients with predetermined patterns. The use of predetermined patterns increases the accuracy of the method.

- the step of identifying an activity associated with a motion unit includes a probabilistic recognition step and/or a deterministic recognition step. The presence of one or more of these steps provides greater certainty in identifying the activity associated with the motion unit.
- the step of identifying at least two key moments is carried out in an electronic box integrated into the sole. This identification step can be carried out in an external electronic device such as a mobile phone or a computer server. Nevertheless, it is preferably carried out in an electronic box integrated into the sole. Similarly, the step of determining an advanced biomechanical gait parameter value is carried out in an electronic box integrated into the sole. Nevertheless, in some cases and for example for some advanced biomechanical parameters, it can advantageously be carried out in an external electronic device.
- it further includes a step of calculating a combinatorial pattern of advanced biomechanical parameter values, said combinatorial pattern of advanced biomechanical parameter values corresponding to a combination of advanced biomechanical parameter values or to a time-dependent behavior combination of advanced biomechanical parameters. Such a combinatorial pattern of biomechanical parameters can be advantageously associated with a physiological state of the user. This is particularly advantageous since it makes it possible to generate new patterns that can be correlated with physiological states or predetermined pathological states and thus access, from a characterization of the gait, risk data for the user.

The invention further relates to a system for determining an advanced biomechanical gait parameter value from data generated by one or more motion sensors of a sole, characterized in that it includes:

- Two sets of one or more motion sensors of a sole, where a first set can be associated with a first sole or shoe and a second set can be associated with a second sole or shoe, each set being configured to generate data including acceleration, angular velocity, and/or magnetic field values; and
- One or more analysis modules configured to determine an advanced biomechanical gait parameter value, said one or more analysis modules being configured to:
  - Acquire the data generated by the one or more motion sensors;
  - Calculate an orientation value of the sole, said orientation value of the sole being calculated with respect to a terrestrial reference frame from data including the acceleration, angular speed, and/or magnetic field values;
  - Identify an activity associated with a motion unit, said identification of an activity including comparing activity reference values with values selected from: acceleration, angular speed, and/or orientation values of the sole, or global descriptive parameter values calculated from the acceleration, angular speed, and/or orientation values of the sole;
  - Identify at least two key moments of the motion unit for which an activity has been identified, said step of identifying key moments including comparing motion parameter values with at least one predetermined threshold, said predetermined threshold being associated with the identified activity and said motion parameter values including acceleration, angular speed, and/or orientation values of the sole; and Determine an advanced biomechanical gait parameter value, said determination including calculating a biomechanical gait parameter value for at least one of the identified key moments and from the acceleration, angular speed, and/or orientation values of the sole.

Furthermore, the set pair of one or more motion sensors of a sole may correspond to a pair of electronic boxes adapted to be integrated into a pair of soles.

It may advantageously include a plurality of processing modules each configured to perform part of the determination of an advanced biomechanical gait parameter value.

Other advantages and features of the invention will appear upon reading the following description given by way of illustrative and non-limiting example, with reference to the appended figures.

Figure 1:
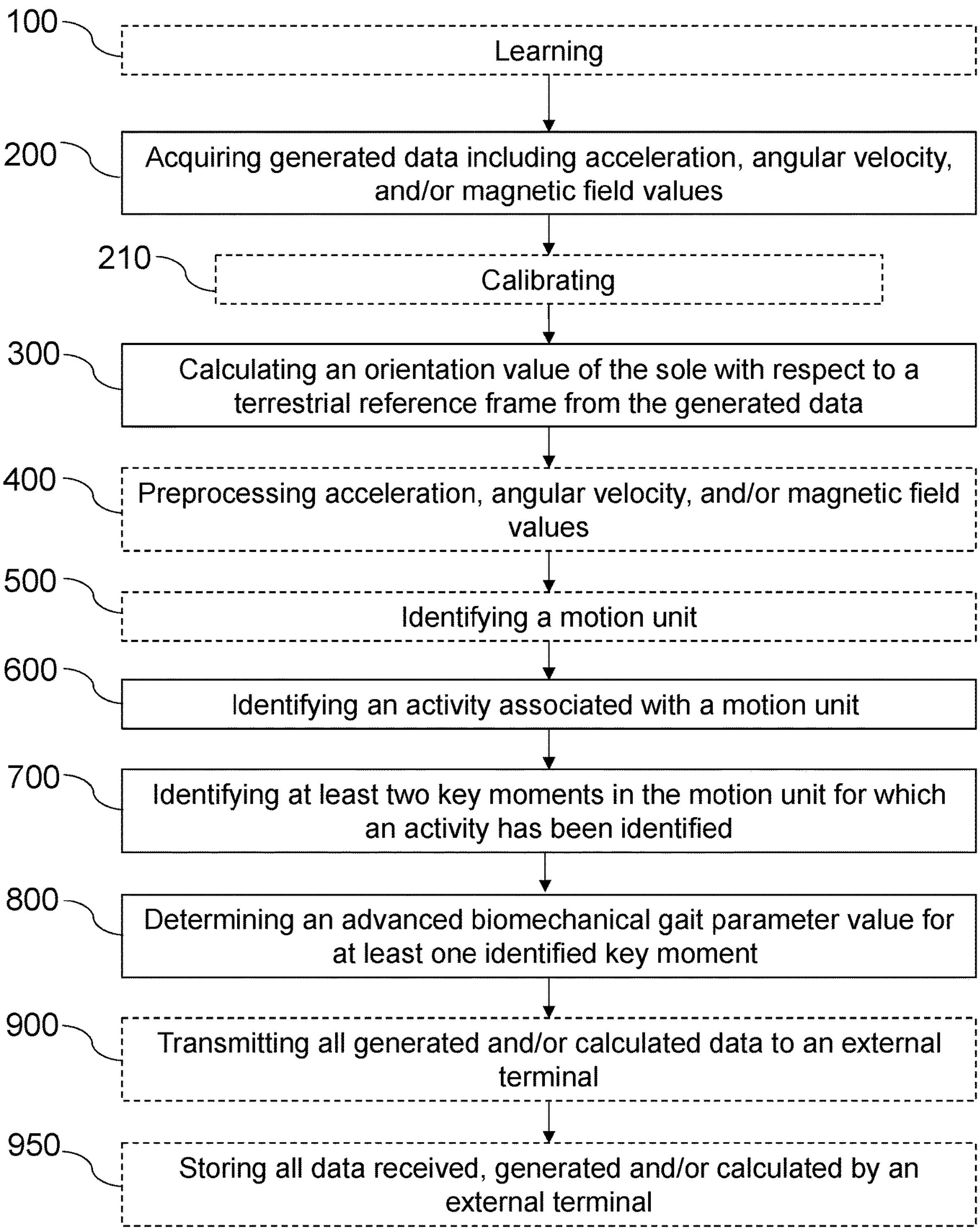
FIG. 1 shows a diagram representative of a method according to an embodiment of the invention.

Aspects of the present invention are described with reference to flowcharts and/or block diagrams of methods, apparatus (systems), and computer program products according to embodiments of the invention.

In the figures, the flowcharts and block diagrams illustrate the architecture, functionality, and operation of possible implementations of systems, methods, and computer program products according to various embodiments of the present invention. In this respect, each block in the flowcharts or block diagrams may show a system, device, module, or code, which comprises one or more executable instructions for implementing the one or more specified logical functions. In some implementations, the functions associated with the blocks may appear in a different order than that shown in the figures. For example, two blocks shown in succession may, in fact, be executed substantially simultaneously, or the blocks may sometimes be executed in reverse order, depending on the functionality involved. Each block in the flow diagrams and/or flowchart, and combinations of blocks in the flow diagrams and/or flowchart, may be implemented by special hardware systems that perform the specified functions or acts or perform combinations of special hardware and computer instructions.

DESCRIPTION OF THE INVENTION

In the following description, "gait", within the meaning of the invention, corresponds to the user's posture, movements, locomotion, and balance. The balance corresponds in particular to the postural balance linked to the stability of the body and more particularly to the stability of the user's center of gravity. However, it can integrate both static and dynamic balance.

The "gait characterization" corresponds, within the meaning of the invention, to the assignment of one or more values, for example a score, a ranking, or a mark to a trajectory or to the movement of a user's foot. This gait characterization allows one or several numerical or alphanumerical values of biomechanical parameters representative of the gait, to be obtained.

By "biomechanical parameter" is meant, within the meaning of the invention, a characteristic of the user's gait. By "advanced biomechanical parameter" is meant, within the meaning of the invention, a characteristic of the user's gait determined at a key moment of a cycle and therefore more complex to determine.

By "sole" is meant an object for separating the user's foot from the ground. A shoe may include an upper sole layer in direct contact with the user's foot and a lower sole layer in direct contact with the ground or more generally the outside environment. A shoe may also include a removable insole.

By "removable" is meant the ability to be detached, removed, or disassembled easily without having to destroy the means of attachment, either because there is no means of attachment, or because the means of attachment can be easily and quickly disassembled (for example notch, screw, tongue, lug, clips). For example, by removable, is to be understood that the object is not attached by welding or any other means not intended to allow the object to be detached.

By "model" or "rule" or "algorithm" is to be understood, within the meaning of the invention, a finite sequence of operations or instructions for calculating a value through a classification or partitioning of the data within predefined groups Y and for assigning a score or ranking one or more data within a classification. The implementation of this finite sequence of operations allows, for example, to assign a label Y to an observation described by a set of characteristics or parameters X, using for example the implementation of a function f likely to reproduce Y, having observed X.

$$Y=f(X)+e$$

where e symbolizes noise or measurement error.

By "supervised learning method" is meant, within the meaning of the invention, a method for defining a function f from a base of n labeled observations ($X_{1 \ldots n}$, $Y_{1 \ldots n}$) where Y=f(X)+e.

By "unsupervised learning method" is meant a method of prioritizing data or dividing a data set into different homogeneous groups, with the homogeneous groups sharing common characteristics and without the observations being labeled.

By "substantially constant" is meant a value varying by less than 30% with respect to the compared value, preferably by less than 20%, even more preferably by less than 10%.

By "process", "calculate", "determine", "display", "transform", "extract", "compare" or more broadly "executable operation" is meant, within the meaning of the invention, an action performed by a device or processor unless the context indicates otherwise. In this regard, the operations relate to actions and/or processes of a data processing system, for example a computer system or an electronic computing device, which manipulates and transforms the data represented as physical (electronic) quantities in the memories of the computer system or other devices for storing, transmitting or displaying information. These operations may be based on applications or software.

The terms or expressions "application", "software", "program code", and "executable code" mean any expression, code, or notation in a set of instructions designed to cause data processing in order to perform a particular function directly or indirectly (for example after an operation of converting into another code). Exemplary program codes may include, but are not limited to, a subprogram, a function, an executable application, a source code, an object code, a library, and/or any other sequence of instructions designed for being performed on a computer system.

By "processor" is meant, within the meaning of the invention, at least one hardware circuit configured to perform operations according to instructions contained in a code. The hardware circuit may be an integrated circuit. Examples of a processor include, but are not limited to, a central processing unit, a graphics processor, an application-specific integrated circuit (ASIC), and a programmable logic circuit.

By "coupled" is meant, within the meaning of the invention, connected, directly or indirectly with one or more intermediate elements. Two elements may be coupled mechanically, electrically, or linked by a communication channel.

In this description and even before, the same references are used to refer to the same elements.

As a reminder, both feet contain a quarter of all the bones in the human body. In each foot, 26 bones, 33 muscles, 16 joints, and 107 ligaments can be identified. The feet bear the weight of the body in the standing position and allow locomotion, playing a key role in balance, damping, and propulsion. Feet also perform several types of movements. In addition, the feet have almost 7200 nerve endings, so that all diseases and other disorders, especially neurological ones, can be detected directly or indirectly in our feet and, on the other hand, can be detected from the way we walk or move.

The inventors have tested several methods to quantify a user's posture and gait. They have selected the systems integrating inertial sensors, which are the most likely to provide a rapid response at a cost that is bearable for industrialization. Indeed, the existing methods are generally based on pressure sensors or on a plurality of sensors distributed in the shoe and/or sole or on the ankle. Such a distribution of sensors leads to a reduction in the robustness of the system.

Nevertheless, most of the tested methods based on inertial sensor data (acceleration and angular velocity) exhibit biases that are too important when calculating certain advanced biomechanical parameter values, which limits their use as criteria for gait characterization.

Indeed, the inventors have highlighted, during tests of the usual inertial platform data processing methods, as have others, a variability in interpersonal and intrapersonal walking that can, when the data processing operations are not adapted, lead to prejudicial biases. In addition, with processing methods using sliding window pattern analyzes from raw data from both feet, power and memory consumption reduced the device's autonomy to a few tens of minutes. This was the case even when the calculations were carried out on telephones, connected watches, or remote servers.

Faced with these shortcomings, the inventor has developed a method 1 for determining an advanced biomechanical gait parameter value from data generated by one or more motion sensors of a sole as shown schematically in FIG. 1.

According to a first aspect, the invention relates to a method for determining an advanced biomechanical gait parameter value. In particular, such a method is implemented by one or more analysis modules. Preferably, by several analysis modules, each configured to perform part of the method.

In particular, such a method is implemented from data generated by one or more motion sensors of a sole, described below. Some of the motion sensors can be distributed in the sole or can be positioned on the shoe so as to follow the movements of the sole. The motion sensors may also all be integrated into a first box associated with a first shoe and a second box associated with a second shoe of the same pair.

As illustrated in FIG. 1, such a method according to the invention includes in particular the following steps: acquiring 200 data generated by one or more motion sensors of a sole, calculating 300 an orientation value of the sole, identifying 600 an activity associated with a motion unit, identifying 700 at least two key moments of the motion unit for which an activity has been identified, and determining 800 an advanced biomechanical gait parameter value.

In addition, a method according to the invention may include advantageous steps such as: learning 100 the user's gait, preprocessing 400 the data generated by the motion sensors and/or the values calculated in the context of the method, identifying 500 a motion unit, transmitting 900 data, or storing 950 data.

Figure 2:
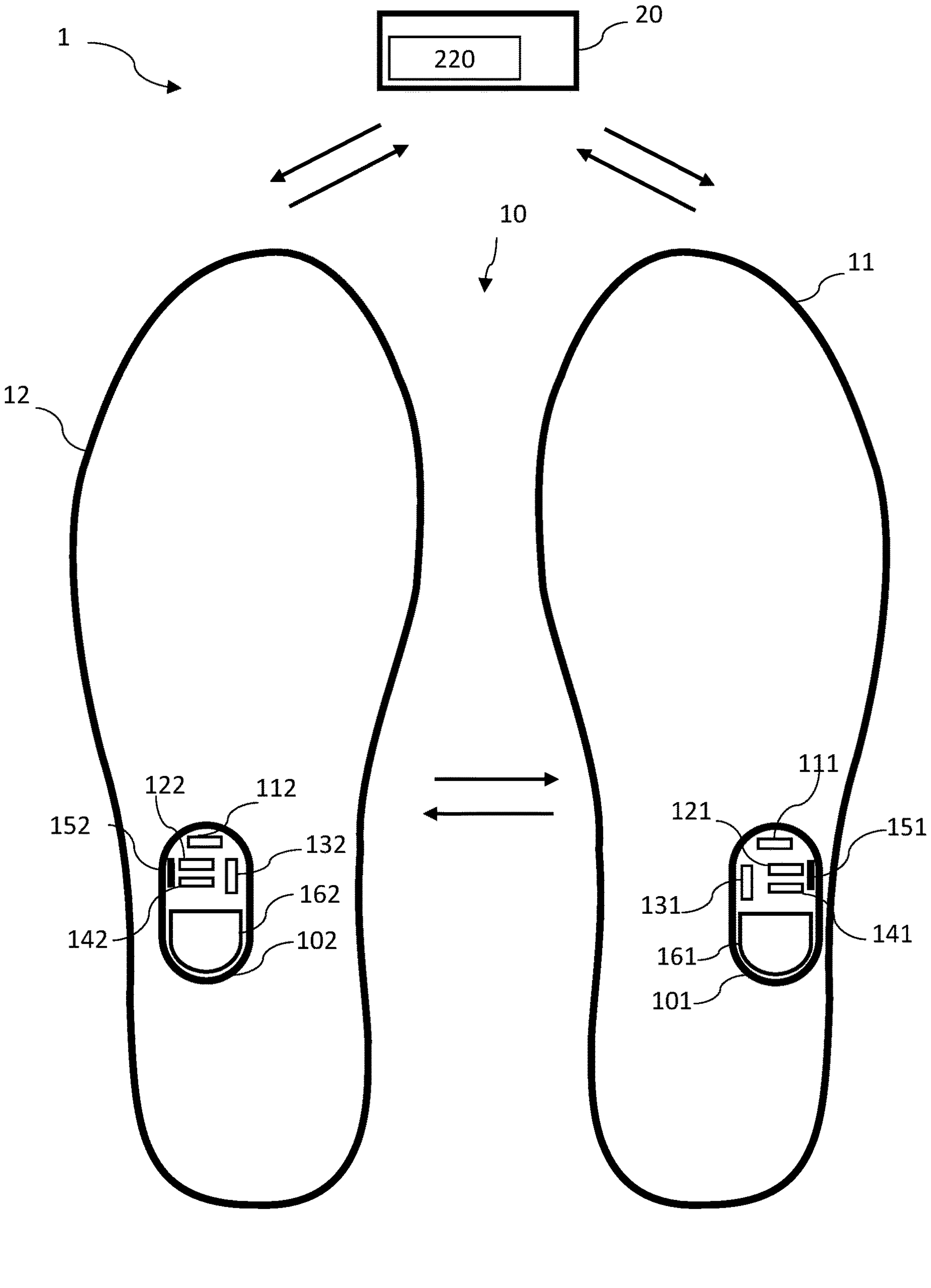
FIG. 2 shows a longitudinal cross-sectional top view of two soles, each containing a cavity which will give way to a box, each of the antennas of the boxes being located on the outer edge facing each foot, according to an embodiment of the invention.

As illustrated in FIG. 2, a method according to the invention may include a step 100 of learning the user's gait. In particular, such a step may include defining a plurality of activity reference values of a user. For example, when repeating movements, postures, and gaits performed by a user over a determined period of time, activity reference values can be recorded and classified according to a plurality of values, including patterns such as static or dynamic patterns.

Thus, a certain dynamic pattern can represent a user's movement such as, by way of non-limiting example, a "step" and a static pattern can, in an advantageous but not limiting manner, represent a user's posture of the "kneeling" type. In particular, the predetermined patterns may have been normalized to a time period corresponding to a cycle, where the cycle may be a walking cycle. There are different types of activities such as stepping, going up a step, going down a step, striding, jumping, flattening, dropping, stomping, kneeling . . . . Therefore, a cycle may also correspond to a plurality of activities of different types depending on the complexity of the movement performed by the user.

This learning step 100 may be implemented when said user uses the motion sensors for the first time and it may also be repeated occasionally so as to increase the accuracy of the step 600 of identifying an activity associated with a motion unit.

Thus, a method in accordance with the invention may include generating reference values, each of which is associated with an activity and more particularly with a set of reference values per activity. The method may then include generating multiple sets of reference values so as to cover several activities of the user. More preferably, the method includes generating at least four sets of reference values.

For example, the activity reference values of a user may be stored in an electronic box, with the right foot reference values being stored in the electronic box associated with the right foot and the left foot reference values being stored in the electronic box associated with the left foot.

The activity reference values of a user may also be transmitted to an external terminal which can store them or transmit them to other terminals.

A method according to the invention includes a step 200 of acquiring data generated by one or more motion sensors of a sole. The acquisition, as can be understood from reading the present description, is preferably carried out for each of the two soles. This step may correspond, in particular in the context of the invention, to the acquisition of data generated by one or more motion sensors of a box or several boxes, for example each integrated into a sole.

In particular, the acquired data includes acceleration, angular velocity, and/or magnetic field values. Preferably, the acquired data includes acceleration, angular velocity, and magnetic field values. This acquisition step may also include acquiring other data such as geolocation data, temperature data, pressure data.

The method according to the invention is based at least in part on data generated by inertial units. Thus, it may include a step of generating raw data from motion sensors of a sole including one or more inertial platforms. This raw data is usually generated for a given period of time and depending on a user's gait.

In particular, the inertial platforms may be contained in a first and a second box. The raw data can thus come from a gyroscope, an accelerometer, and a magnetometer, for example contained in each box. In addition, according to an advantageous embodiment, the raw data is collected by the two boxes over a predetermined period of time which may, for example, range from one millisecond to several hours.

Preferably, the motion sensors, preferably the electronic boxes, are configured to communicate with each other and to initiate the generation of data for the motion only after a message from the other electronic box is received by a first electronic box. Thus, the generation of data by the inertial platforms, for example of the two boxes, is preferably synchronized, which allows a finer and more accurate analysis of the user's gait. In the absence of such synchronization, the fusion of the advanced biomechanical parameters calculated from data from the first box will not be possible with high accuracy with advanced biomechanical parameters calculated from data from the second box to calculate new advanced biomechanical motion parameters.

In particular, a method according to the invention may comprise a calibration step 210, between a first and a second set of motion sensors. As will be described below, each of the sets of motion sensors may be associated with a shoe and may take the form of a first and a second electronic box.

The calibration step may include transmitting a signal from the first set of motion sensors and receiving the signal from the second set of motion sensors in order to calibrate a time measuring means, preferably a clock. Such a calibration allows the first and the second box to detect and collect posture or gait data of a user over the same time window. Indeed, the data collected by the first and the second box can be analyzed two by two in particular for some advanced biomechanical gait parameters. Thus, the data collected will be analyzed in parallel, thus avoiding any discrepancy between the data and any analysis errors.

A method according to the invention also includes a step 300 of calculating an orientation value of the sole.

The orientation of the sole corresponds in particular to the angular positions of the sole along three orthogonal axes x, y, and z. Thus, preferably, the step 300 of calculating an orientation value of the sole allows the calculation of an angular position value for each of the three axes x, y, and z.

The orientation value of the sole can be calculated with respect to a terrestrial reference frame and from data including acceleration, angular velocity, and/or magnetic field values. In particular, it can be calculated from the acceleration, angular velocity, and magnetic field values.

Many algorithms, such as fusion algorithms, may be used to calculate the orientation value of the sole.

For example, a method in accordance with the invention may implement an algorithm for the fusion of accelerometer, gyroscope, and magnetometer data based on filters coupled with probabilistic models. Alternatively, a method in accordance with the invention may implement an algorithm for the fusion of accelerometer and gyroscope data based on filters coupled with probabilistic models.

Such a method may also implement a Kalman-type filter algorithm and its variants. Thus, for example, a linear Kalman filter, an extended Kalman filter, an additive extended Kalman filter, a multiplicative extended Kalman filter, a cubing Kalman filter, or a particle filter may be used.

Alternatively, a method according to the invention may also implement a Premerlani & Bizard fusion algorithm, a Mahony fusion algorithm, or a Madgwick fusion algorithm.

In addition, such a method may implement rotation matrices formed based on direction cosines or quaternions.

A method according to the invention may include a step 400 of preprocessing data generated by one or more motion sensors of a sole. In addition, this preprocessing step may involve values calculated in the context of the implementation of a method according to the invention, such as the orientation values of the sole.

In particular, this preprocessing step may correspond to preprocessing the acceleration, angular velocity, and orientation values of the sole. For example, it may include in particular at least one processing selected from: frequency filtering, suppression of gravity on acceleration values, suppression of gravity, suppression of noise on acceleration values, and suppression of drift on the angular velocity and/or orientation values of the sole.

Figure 5:
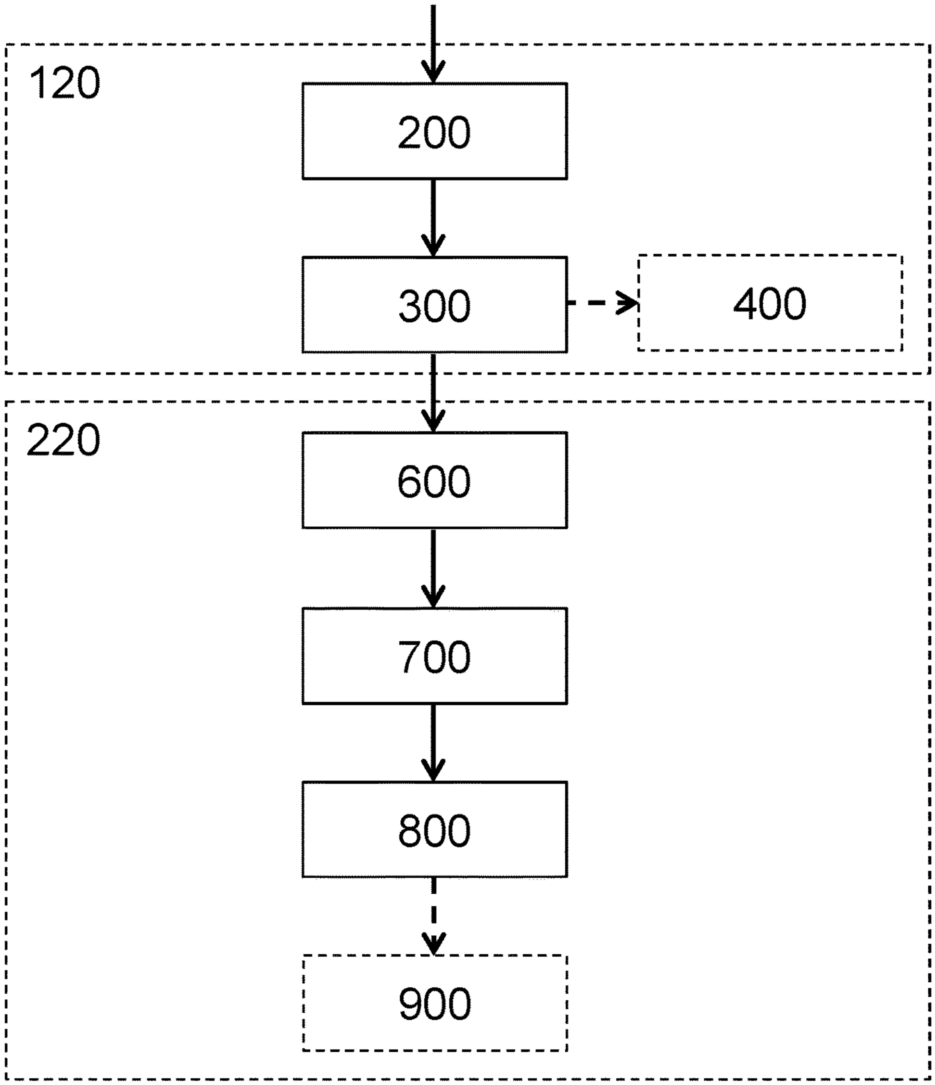
FIG. 5 shows a diagram representative of a method according to an embodiment of the invention where part of the calculations are carried out in electronic boxes associated with shoes, for example integrated into soles.

As illustrated in FIG. 5, this preprocessing step 400 may be implemented by data processing modules contained in the motion sensors and more particularly in the first and the second box.

Alternatively, this preprocessing step 400 may be implemented by a data processing module contained in an external terminal 20.

A method according to the invention may also include a step 500 of identifying a motion unit. The motion unit, within the meaning of the invention, corresponds to a walking cycle, a running cycle, or a stair climbing cycle.

These cycles may be defined as the period of time from the initial contact of a foot to the next occurrence of the same event with the same foot.

In the context of the invention, many partitioning methods may be used. Thus, this step may for example include the implementation of conventional steps for studying the movement of the step such as the Pan-Tompkins method or the detection of thresholds, maxima, and/or minima.

A method according to the invention also includes a step 600 of identifying an activity associated with a motion unit.

This identification may for example be carried out by a processing module of an external terminal. Such a step allows the data to be filtered in order to calculate in the next steps advanced biomechanical parameters only on qualified/confirmed motion units. Thus, the accuracy of the measurement is improved.

This identification of an activity preferably includes comparing activity reference values with values selected from: acceleration, angular velocity, and/or orientation values of the sole, or global descriptive parameter values calculated from the acceleration, angular velocity, and/or orientation values of the sole.

The activity reference values may be the activity reference values generated in the learning step 100, for example in the case of deterministic recognition and/or predetermined activity reference values for example in the case of probabilistic recognition.

The global descriptive parameters calculated from the acceleration, angular velocity, and/or orientation values of the sole may be, for example, a variance, a mean, a median, a kurtosis, or a skewness coefficient.

In particular, the step 600 of identifying an activity associated with a motion unit includes calculating one or more global descriptive parameters from the acceleration, angular velocity, and/or magnetic field values, for example from the acceleration and angular velocity values or from the acceleration, angular velocity, and magnetic field values. With the global descriptive parameters preferably including a kurtosis or skewness coefficient value. Nevertheless, the global descriptive parameters may have other values or coefficients. For example, the global descriptive parameters may preferably correspond to values of similarity coefficients with predetermined patterns.

In addition, the step 600 of identifying an activity associated with a motion unit may include a probabilistic recognition step and/or a deterministic recognition step.

Preferably, the step 600 of identifying an activity associated with a motion unit includes a probabilistic recognition step and a deterministic recognition step. Indeed, deterministic recognition allows to adhere as best as possible to the movement of the person, and probabilistic recognition allows to easily enrich the possibilities of recognition so as to allow adaptation to the user's need.

The probabilistic recognition stage is based on pre-established models and the identification of the activity then incorporates a calculation of the probability that a motion unit corresponds to one activity rather than another.

The probabilistic recognition includes, for example, a sub-step of calculating global descriptive parameters for describing the movement of the sole, a sub-step of comparing the calculated global descriptive parameters to a predefined training model, and an identification of the activity according to the results of the comparison.

The pre-established learning model may, for example, be established via supervised or unsupervised approaches. Among the supervised learning methods, neural networks, classification trees, or regression trees are among the most robust and efficient machine learning techniques in the context of the method according to the invention.

For example, it is possible to use a supervised learning step to teach trees to classify motion units according to an associated activity. To this end, the method preferably includes a preliminary step of receiving labeled (with the associated activity) values such as acceleration, angular velocity, and/or orientation values of the sole, or global descriptive parameter values calculated from the acceleration, angular velocity, and/or orientation values of the sole.

In a preferred embodiment, a supervised learning is used to train a CART ("Classification And Regression Trees" in Anglo-Saxon terminology)-type algorithm. The CART-type algorithm may then be configured to predict the activity from the selected values and to calculate a confidence interval or prediction error. Alternatively, a neural network of the LSTM ("Long short-term memory" in Anglo-Saxon terminology) type may also be used to establish the pre-established learning model.

The deterministic recognition step is based on reference movements made by the user during the learning step. The deterministic recognition step may then integrate the generation of a resemblance score.

In addition, the step 600 of identifying an activity associated with a motion unit may include a step of calculating a similarity value between each of the activity reference values and the values selected for identification.

Thus, the step 600 of identifying an activity associated with a motion unit may include making a classification between the reference values so as to determine the one or more activities that may correspond to the motion unit studied, on the one hand, and the degree of similarity, on the other hand. In addition, the identification step 600 may include a step of validating the motion unit when the latter allows the generation of a similarity value exceeding a predetermined threshold.

A similarity value may be calculated for the data generated from the first and the second box. These calculations may, for example, be carried out by an external terminal 20. Advantageously, since the data is synchronized, a similarity value is calculated, for a same period of time, a first time for the data of the first box and a second time for the data of the second box. Thus, it is possible to quantify a user's posture or gait more reliably and with improved accuracy.

Thus, the method may include a step of selecting an activity representative of a motion unit from the similarity values. In particular, this step comprises selecting an activity if, for a same time point and given that the data measurements are preferably synchronized, a first activity representative of a motion unit of a first set of sensors is identical to a second activity representative of a motion unit of a second set of sensors. This allows data to be taken from both feet before selecting an activity and further increases the accuracy of the method.

In addition, if no similarity value exceeds a predetermined threshold, the method may involve disregarding this motion unit as it does not correspond to a well-characterized activity and is therefore likely to bring inaccuracy to the measurements of advanced biomechanical parameters carried out.

The method according to the invention includes a step 700 of identifying at least two key moments of the motion unit for which an activity has been identified.

In particular, the step of identifying key moments includes comparing the orientation values of the sole to at least one predetermined threshold. Preferably, the at least one predetermined threshold is associated with the identified activity. Thus, depending on the activity identified, the one or more predetermined thresholds may be modified so as to allow for a finer analysis and a more accurate calculation of advanced biomechanical parameter values.

While most prior art methods seek to determine predetermined thresholds or algorithms for accommodating all cycles, the present invention is based on a combination of activity identification with a selection of key moments based on one or more predetermined thresholds specifically adapted to that activity.

A predetermined threshold associated with an identified activity may, for example, correspond to the identification of a predetermined value being exceeded or the identification of a change from a positive value to a negative value or the identification of a particular pattern of a series of values indicative of a key moment. Thus, a predetermined threshold may correspond to the identification of a second local minimum, a local maximum, or a sequence of a local minimum and a maximum.

The motion parameter values include, for example, the acceleration, angular velocity, and/or orientation values of the sole.

As part of this step 700 of identifying at least two key moments of the motion unit, many partitioning models, each with different levels of granularity, may be used. For example, it is possible to divide the movement into two main phases, namely posture and tilting. Nevertheless, it is possible to split into a larger number of phases. For example, three, four, five, six, or more phases may be considered to accommodate particular uses.

Preferably, the method includes a step 700 of identifying at least four key moments of the motion unit for which an activity has been identified. The moment of impact corresponds to the precise moment the foot (for example heel) contacts the ground, the toes touch the ground, the heel lifts off the ground, and the toes lift off the ground. Such key moments allow phases to be identified such as the support phase (takes place from the impact phase until the heel lifts off the ground), the propulsion phase (begins when the heel has left the ground and ends when the first toe has left the ground), and the flight phase (begins when the first toe has left the ground and ends when the heel touches the ground).

The method also includes a step 800 of determining an advanced biomechanical gait parameter value.

Preferably, the determination includes calculating a biomechanical gait parameter for at least one of the identified key moments from the acceleration, angular velocity and/or orientation values of the sole. The calculation may be done from the acceleration, angular velocity, and/or orientation values of the sole which may be transformed (for example filtered, corrected . . . ).

The advanced biomechanical gait parameter may advantageously be selected from: propulsion speed, fatigue rate, Fick angle, propulsion direction, and deceleration direction.

In particular, the determination may include calculating, for at least one identified key moment, a velocity value of the sole from the acceleration values at said at least one identified key moment. Preferably, the determination may include calculating, for at least one identified key moment, a velocity value of the sole from the acceleration values at said at least one identified key moment and said identified key moment corresponds to the toes lifting off the ground. Thus, the method according to the invention makes it possible to calculate the propulsion speed, preferably at each of the user's feet.

Such a propulsion speed, when the toes lift off the ground, is a key biomechanical parameter in the characterization of the gait and is not suggested by the existing procedures.

The Fick angle corresponds in particular to the opening angles in relation to the direction of walking and between the two feet. The Fick angle in the context of the present invention corresponds to the values calculated for at least two key moments, preferably at least three key moments, and even more preferably four key moments.

The direction of propulsion corresponds in particular to the angle between the direction of lifting-off the ground and the axis of the foot when the toes lift off the ground. The direction of propulsion in the context of the present invention corresponds to the values calculated for at least two key moments, preferably at least three key moments, and even more preferably four key moments.

In particular, the direction of deceleration corresponds to the angle between the direction of deceleration and the axis of the foot when the heel touches the ground. The direction of deceleration in the context of the present invention corresponds to the values calculated for at least two key moments, preferably at least three key moments, and even more preferably four key moments.

Furthermore, it has been determined in the context of the present invention that the relationship between the propulsion speed (for example when the toes lift off the ground) and the speed of the sole during a flight phase is indicative of the user's fatigue. Thus, a method according to the invention also includes calculating a fatigue rate, with said fatigue rate corresponding to a ratio between the propulsion speed and the speed of the sole during the flight phase.

In addition, the method according to the invention may also include a step of calculating values of new advanced biomechanical gait parameters from values of advanced biomechanical gait parameters obtained from a first set of motion sensors associated with the right foot and values of advanced biomechanical gait parameters obtained from a second set of motion sensors associated with the left foot.

Thus, the method according to the invention makes it possible to calculate, from the signals generated by inertial platforms, accurate advanced biomechanical parameters, representative of the user's gait. As will be detailed hereafter, calculating these advanced biomechanical parameters may be done partly in an electronic box embedded in a sole but also entirely in an external terminal. Alternatively, calculating these advanced biomechanical parameters may be done entirely in one or more embedded electronic boxes.

More preferably, the method according to the invention may be used to calculate the values of at least one, for example at least two, of the following biomechanical parameters: stability of the foot during the flight phase, step roll-forward, step length, step width, step angle, stride length, and/or stride width.

This constitutes a list of various biomechanical parameters, and the invention is not limited to the calculation of these particular parameters. Indeed, from the data generated by the inertial platforms, the invention allows a plurality of different biomechanical parameters to be calculated, the list of which is limited only by their usefulness for the user.

For example, the method may be used to calculate a propulsion orientation value. This biomechanical parameter corresponds more particularly to the angle of a foot, for example in relation to the ground, during the propulsion phase. Similarly, the method may be used to calculate a value for many other biomechanical parameters.

In addition, in the context of the present invention, the method according to the invention may include a step of calculating a so-called synchronized biomechanical parameter value. Within the meaning of the invention, a so-called synchronized biomechanical parameter is a biomechanical parameter, the calculation of which requires data from two sets of motion sensors, each associated with a sole of a pair of shoes. For example, in this context, the method includes a step of calculating a so-called synchronized biomechanical parameter value from one or more biomechanical parameters calculated by the first electronic box and one or more biomechanical parameters calculated by the second electronic box. This embodiment is particularly advantageous because it allows access to fine characterizations of the gait.

In addition, in the context of the present invention, the method according to the invention may include a step of calculating a combinatorial pattern of biomechanical parameters. Within the meaning of the invention, a combinatorial pattern of biomechanical parameters corresponds to a combination of biomechanical parameters (that is to say values) or to a combination of behavior as a function of time of biomechanical parameters. Such a combinatorial pattern of biomechanical parameters may be advantageously associated with a physiological state of the user. This embodiment is particularly advantageous because it makes it possible to generate new patterns that may be correlated with physiological states or predetermined pathological states and thus access, from a characterization of the gait, risk data for the user. Alternatively, calculating a combinatorial pattern of biomechanical parameters and then comparing thereof may be done by the processing module carried by an external terminal.

A combinatorial pattern of biomechanical parameters may, for example, include a combination of a pace value, a stride length value, and a walking speed. Such a combinatorial pattern of biomechanical parameters makes it possible, from the individual values of each of these three parameters, to determine a walking disorder which may, for example, be caused by an aggravation of a Parkinsonian step.

In addition, the method according to the invention may be configured to calculate skewness between the biomechanical parameters of a right leg with respect to the biomechanical parameters of a left leg.

In addition, the method according to the invention may be configured to calculate a variability of biomechanical parameters associated with one leg or both legs.

Advantageously, the method according to the invention includes a profiling step consisting in establishing a profile of the user during a first period of use. This first period of use may, for example, last a day, a week, or a month. A first period of use preferably has a sufficient duration to calculate a set of advanced biomechanical gait parameters stable over time with preferably low variability (for example less than 20%, preferably less than 10%). It usually takes a few days to a few weeks to build a user's profile.

Advantageously, if one of the boxes were to disconnect or lose time synchronization with respect to the other box, the method comprises a step of synchronizing the boxes. Thus, a search signal is sent by the connected box, the disconnected box receives the search signal and synchronizes with the connected box.

Preferably, the method may also include a step of transmitting 900 data to an external terminal. This transmission is preferably made on an ad hoc basis. In particular, this may correspond to the transmission of all generated and/or calculated data to an external terminal.

In particular, the transmission can be carried out by a communication module of the electronic boxes.

In addition, the method may involve transmitting the data received by the external terminal to one or other external terminals that may be involved in calculating the advanced biomechanical gait parameter values or in displaying thereof.

The transmitted data may for example be raw data as generated by the motion sensors, preprocessed data, or calculated data such as orientation values of the sole.

The method may also include a step of storing 950 the advanced biomechanical gait parameter value. It may also include storing the values generated by the motion sensors, preprocessed data, or calculated data such as the orientation values of the sole. In particular, this may correspond to storing all data received, generated, and/or calculated by an external terminal.

Advantageously, as opposed to raw and/or preprocessed data which are stored over a short period (for example less than 5 minutes) for example on a cache memory, an advanced gait parameter value is stored for a longer period of time, for example on a memory.

Advantageously, calculating one or more advanced biomechanical gait parameter values is done in real time, that is to say less than 1 hour after the data have been generated by the one or more motion sensors of a sole, preferably less than 10 minutes, more preferably less than 1 minute, even more preferably less than 10 seconds.

According to another aspect, the invention relates to a system 1 for determining an advanced biomechanical gait parameter value from data generated by one or more motion sensors of a sole.

Preferably, such a system includes modules configured to carry out a method according to the invention and its various embodiments, whether preferred, advantageous, or not.

In particular, the system according to the invention includes two sets of one or more motion sensors of a sole 101, 102, and one or more analysis modules 120, 121, 122, 220 configured to determine an advanced biomechanical gait parameter value.

Preferably, the first set is adapted to be associated with a first sole and a second set is adapted to be associated with a second sole, each set being configured to generate data including acceleration, angular velocity, and/or magnetic field values.

Preferably, the system includes several analysis modules, where two analysis modules 120, 121, 122 may be associated at the shoe with the motion sensors, for example within two electronic boxes and another analysis module 220 may be associated with an external terminal 20.

These analysis modules are configured to perform the following actions together:

- Acquire the data generated by the one or more motion sensors;
- Calculate an orientation value of the sole, said orientation value of the sole being calculated with respect to a terrestrial reference frame from data including the acceleration, angular velocity, and/or magnetic field values;
- Identify an activity associated with a motion unit, said identification of an activity including comparing activity reference values with values selected from: acceleration, angular velocity, and/or orientation values of the sole, or global descriptive parameter values calculated from the acceleration, angular velocity, and/or orientation values of the sole;
- Identify at least two key moments of the motion unit for which an activity has been identified, said step of identifying key moments including comparing motion parameter values to at least one predetermined threshold, said predetermined threshold being associated with the identified activity and said motion parameter values including the acceleration, angular velocity, and/or orientation values of the sole; and
- Determine an advanced biomechanical gait parameter value, said determination including calculating a biomechanical gait parameter value for at least one of the identified key moments and from the acceleration, angular velocity, and/or orientation values of the sole.

These actions can be carried out in redundancy between the different analysis modules.

In particular, the system 1 according to the invention may include a pair 10 of soles including the electronic boxes 101, 102 according to the invention and possibly an external terminal 20.

The soles 11, 12 which can be used in the context of the system 1 according to the invention may, for example, correspond to outsoles or insoles, of shoes. These soles may be removable or be permanently integrated into the sole assembly of the shoes.

Conventionally, the soles 11, 12 constituting said pair 10 of soles, each include an electronic box 101, 102. As shown in FIG. 2, the electronic box 101, 102 is preferably positioned at a midsole portion.

Figure 3:
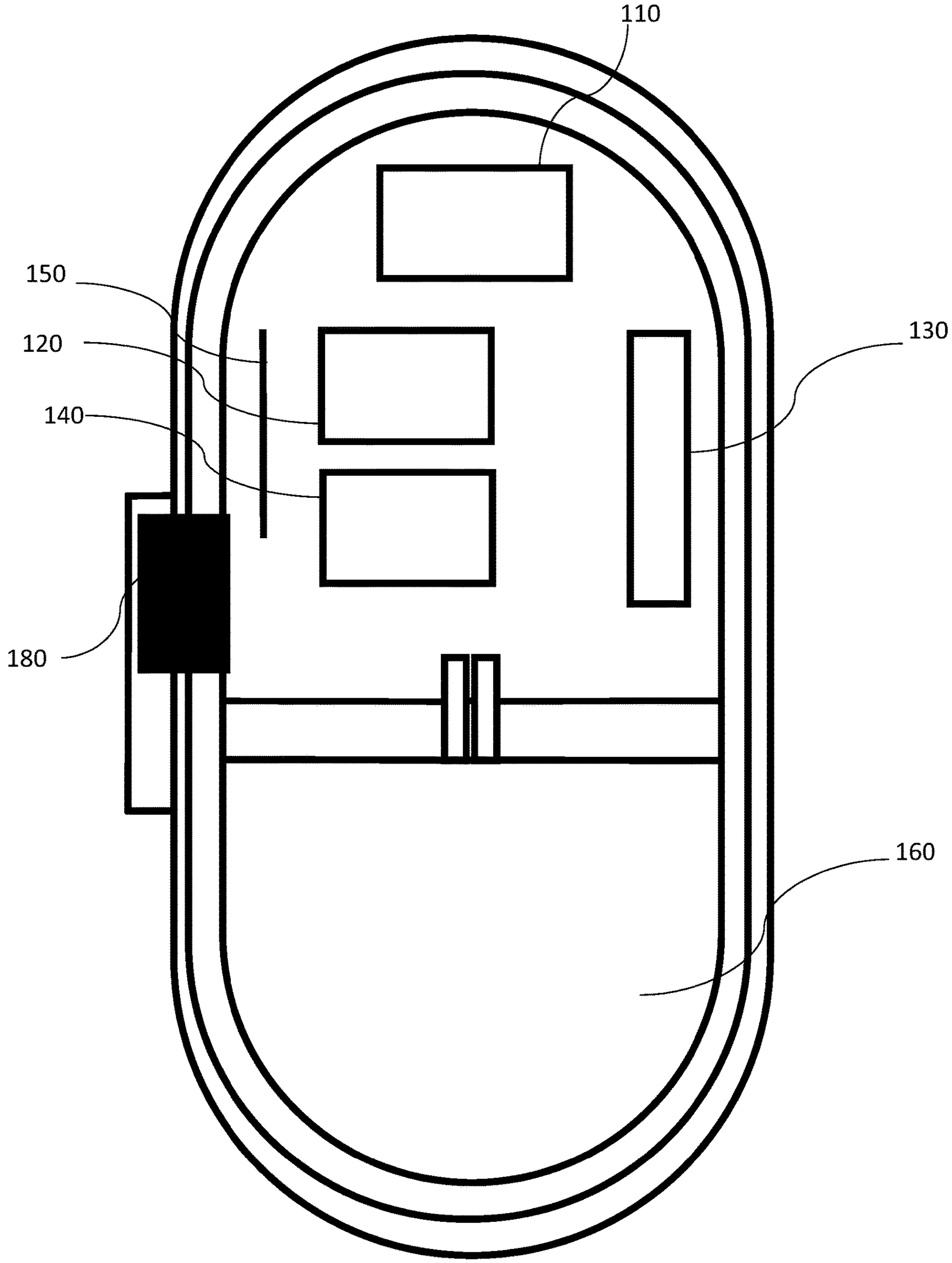
FIG. 3 shows an open electronic box as seen from above comprising in particular an electronic board, a rechargeable battery, a connector, and an antenna.
Figure 4:
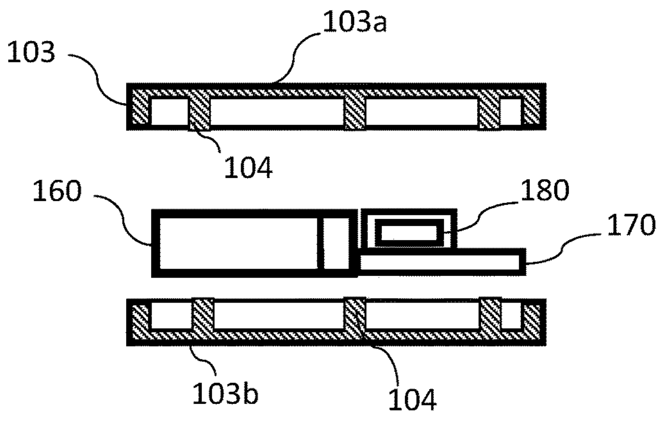
FIG. 4 shows an electronic box, in exploded and profile section view, comprising in particular a rechargeable battery, an electronic board, as well as a two-part outer casing.

An electronic box according to the invention is detailed in FIG. 3. Weighing only a few grams and being of a small size, this electronic box fits into any insole and/or outsole in a space-saving manner. This low volume limits the impact on user comfort and has the advantage of optimizing production costs by making it cheaper and easier to integrate this technology into the sole during the industrial process.

In addition, the electronic box according to the invention includes an inertial platform 110,111,112 configured to generate a set of data on the gait of a user of the pair 10 of soles.

When a user is walking, the inertial platform 110 acquires signals representative of a motion parameter (acceleration and/or speed, for example angular velocity) of the foot along the X, Y, Z axes. In addition, this data may then be processed to generate at least one acceleration signal. The inertial platform consists, for example, of at least one accelerometer and one gyroscope. Preferably, it includes several accelerometers and gyroscopes. The electronic box may also include one or more magnetometers so as to acquire three additional raw signals corresponding to the values of magnetic fields on three dimensions.

Each electronic box may further include other sensors, including an inclinometer, a barometer, a temperature sensor, and an altimeter for increased accuracy.

In addition, the electronic box according to the invention includes a data processing module 120,121,122 which can be configured to transform all of the data generated using predefined algorithms.

This processing module, integrated into the electronic box, may be used to preprocess the data generated by the motion sensors and generate the orientation values of the sole. Then, this data may be sent to an external terminal 20 as shown in FIG. 5 to generate the advanced biomechanical gait parameter values.

Alternatively, as shown in FIG. 6, the processing module, integrated into the electronic box, may be used to acquire the data generated by the motion sensors and send them to an external terminal 20 to generate the advanced biomechanical gait parameter values.

Thus, the electronic box according to the invention includes a data storage module 130,131,132, configured to store at least part of the transformed data and/or of the data generated by the processing module. The system according to the invention is such that it allows operation with a low-capacity data storage module. It may be configured to store the data generated by the inertial platform. Advantageously, the data storage module 130,131,132 is configured to store at least part of the transformed data, but not to store the generated data. Thus, its capacity is not burdened by the raw data generated. The transformed data may correspond to data preprocessed by the processing module or to biomechanical parameters.

In addition, the electronic box according to the invention includes means of communications. Thus, in particular, each of the boxes, whether Slave or Master, is designed so as to be able to communicate independently with the other and/or directly with the terminal in order to be able to exchange its own information on posture/movement/activity of its foot, the data of which it has received via the various sensors of its insole and/or outsole of the shoe.

Preferably, the electronic box according to the invention includes a first means of communication 140,141,142 configured so that the electronic box 100 of at least one of the soles is capable of transmitting at least part of the data to an external terminal 20. These data may be transmitted in real time or in delayed mode to an external terminal 20. The external terminal 20 may, for example, be a remote system such as a tablet, a mobile phone ("smartphone" in Anglo-Saxon terminology), a computer, or a server.

Advantageously, each electronic box further includes a second means of communication configured so that the electronic box 101 of a first sole is able to communicate with the electronic box 102 of a second sole. In particular, both electronic units are configured to communicate with each other and to initiate the generation of data on the movement of a user's foot only after receiving a message from the other electronic box.

The first and second means of communication may consist of one and the same means.

The first and second means of communication are adapted to receive and transmit the data over at least one communication network. Preferably, the communication is operated via a wireless protocol such as WiFi, 3G, 4G, and/or Bluetooth. Preferably, the communication protocol is a BLE or ANT+ protocol. These communications protocols allow for low energy consumption.

Advantageously, because of its confinement inside a box placed under the body of a person, the antenna should preferably be placed inside the box on the side facing the outside of the sole. This positioning of the antenna is preferable since laboratory tests have shown that 70% of the signal emitted from a sole or a shoe is absorbed by the human body. This antenna must therefore be positioned at the periphery of the foot and oriented in such a way that the signal can always be transmitted to the external terminal and/or the box of the second sole. Preferably, the antenna may be an antenna printed on an electronic card. Alternatively, the antenna may be printed on an inner side of the box and connected to the electronic board by wiring. The antenna may preferably be positioned on a lower part in relation to the electronic board. Thus, the electronic board comes into contact with the antenna.

In addition, the electronic box according to the invention includes a power source 160,161,162. The power source is preferably of the battery type, rechargeable or not. Preferably, the power source is a rechargeable battery. In addition, it can be combined with a system for recharging by movement or with external energy. In particular, the system for recharging with external energy may be a wired recharging system, an induction recharging system, or a photovoltaic system.

In addition, the electronic box according to the invention may include a wired connection means 160, preferably protected by a removable tab. This wired connection means may be, for example, a USB or FireWire port. Advantageously, the USB port is also water- or humidity-resistant. In addition, the USB port is advantageously surmounted by a polymer joist to give it greater resistance in use. This wired connection means may be used as mentioned above to recharge the battery, but also to exchange data and for example to update the firmware of the electronic board carrying the various components of the electronic box.

Preferably, the removable tab or USB cover allows the USB port to be protected from foreign bodies. For example, the removable tab can be used to protect the USB port from water or dust. Such a tab may preferably be made of an elastomer or polyurethane type polymer.

These various components of the electronic box are preferably arranged on an electronic board 170 (or printed circuit). In addition, the various means and modules of the electronic box are shown separately in FIGS. 2 and 3, but the invention may provide for various types of arrangement such as a single module combining all of the functions described here. Similarly, these means may be divided into several electronic boards or grouped together on a single electronic board. In addition, when action is taken to a device, a means, or a module, it is actually performed by a microprocessor in the device or module controlled by instruction codes stored in a memory. Similarly, if an action is taken to an application, it is actually performed by a microprocessor in the device, in a memory of which the instruction codes corresponding to the application are stored. When a device or module sends or receives a message, this message is sent or received by a communication interface.

In addition, the system 1 includes an external terminal 20 adapted to receive data. The external terminal 20 is usually a tablet, a mobile phone ("smartphone" in Anglo-Saxon terminology), a gateway, a router, a computer, or a server. It may be able to transfer this data to a remote server. It is then possible, for example, to access this remote server via a web interface.

Thus, the user can access data related to his/her daily physical activities and related to several biomechanical parameters, such as posture, pronation/supination, impact force, step length, contact time, limping, balance, and several other parameters related to the user and describing his/her movements, walk, postures, and movements, and thus follow their evolution.

Advantageously, a dedicated application is installed on this external terminal in order to process the information transmitted by the boxes and allow the interaction of the user with the invention. It is then possible, for example, to access this remote server via a web interface. All communications with the remote server may be secured, for example by HTTPS protocols and AES 512 encryption. Thus, this may allow, via a client, access to data by medical staff in charge of monitoring the user.

In addition, the electronic box according to the invention includes a power source 160, 161, 162. The power source is preferably of the battery type, rechargeable or not. Preferably, the power source is a rechargeable battery. Recharging can be done using different technologies such as:

- by a charger, with a connector flush with the sole;
- with a mechanical recharging device integrated into the sole, such as a piezoelectric device capable of supplying electrical energy from walking;
- with a contactless device, for example by induction; and/or
- with a photovoltaic device.

In addition, the electronic box according to the invention may include a wired connection means 180, preferably protected by a removable tab. This wired connection means may be, for example, a USB or FireWire port. This wired connection means may be used as mentioned above to recharge the battery, but also to exchange data and for example to update the firmware of the electronic board carrying the various components of the electronic box.

Advantageously, the system 1 is configured to implement the biomechanical parameter values in one or more algorithms, preferably calibrated beforehand. These algorithms may have been built from different learning models, in particular partitioning, supervised, or unsupervised models. An unsupervised learning algorithm may, for example, be selected from an unsupervised Gaussian mixture model, a hierarchical bottom-up classification (Hierarchical clustering Agglomerative in Anglo-Saxon terminology), a hierarchical top-down classification (Hierarchical clustering divisive in Anglo-Saxon terminology). Alternatively, the algorithm is based on a supervised statistical learning model configured to minimize a risk of the ordering rule and thus allowing more efficient rules to be obtained. In this case, the calculation, determination, and estimation steps may be based on a model, trained on a data set, and configured to predict a label (for example gait similar or dissimilar to the recorded gait). For example, for calibration purposes, it is possible to use a data set that is representative of a situation with a known label, such as biomechanical parameters characteristic of Parkinson's disease. The data set may also comprise multiple labels. The algorithm may be derived from the use of a supervised statistical learning model selected, for example, from kernel methods (for example Large Margin Separators—Support Vector Machines SVM, Kernel Ridge Regression), set methods (for example decision trees), hierarchical partitioning, k-mean partitioning, decision trees, logical regression, or neural networks.

In addition, the external terminal 20 may include:

- an alert module adapted to alert the user, and possibly medical staff, of an abnormal evolution of one or more biomechanical parameters that may correspond to the onset or an increased risk of the onset of one or more pathologies,
- a communication module adapted to directly contact and inform a health professional, or any other person selected, and previously indicated by the user in the application and/or adapted to regularly provide the user with information related to his/her daily activity and the evolution of the biomechanical parameters over time,
- a corrective module adapted to propose, for example via the external terminal, solutions to rectify or prevent malformation by proposing physical exercises or corrective inserts to be integrated under the foot,
- a prognosis module adapted to measure the effect, and possibly the effectiveness, of a neurological, medical, or other treatment protocol by monitoring the evolution of all or part of the walking parameters via, for example, the value representative of the evolution of the user's gait and adapted to communicate to the user or directly to his/her doctor or any other predetermined person all or part of the observed evolutions of the data collected from said user's gait.

The invention claimed is:

1. A method for determining an advanced biomechanical gait parameter value from data generated by one or more motion sensors of a sole, said method, performed by one or more analysis modules included in an electronic box integrated in the sole, the electronic box having the one or more motion sensors and the one or more analysis modules, the method comprising:

- a step of acquiring data generated by the one or more motion sensors of the sole, said data including acceleration, angular velocity, and/or magnetic field values;
- a step of calculating an orientation value of the sole, said orientation value of the sole being calculated with respect to a terrestrial reference frame from data including acceleration, angular velocity, and/or magnetic field values;
- a step of identifying an activity associated with a motion unit, said identification of the activity including comparing activity reference values with values selected from: acceleration, angular velocity, and/or orientation values of the sole or global descriptive parameter values calculated from the acceleration, angular velocity, and/or orientation values of the sole;
- a step of identifying at least two key moments of the motion unit for which the activity has been identified, said step of identifying key moments including comparing motion parameter values to at least one predetermined threshold, said predetermined threshold being associated with the identified activity and said motion parameter values including the acceleration, angular velocity, and/or orientation values of the sole; and a step of determining an advanced biomechanical gait parameter value, said determination including calculating a biomechanical gait parameter value for at least one of the identified key moments and from the acceleration, angular velocity, and/or orientation values of the sole.

2. The method according to claim 1, wherein the advanced biomechanical gait parameter is selected from: propulsion speed, fatigue rate, Fick angle, propulsion direction, and deceleration direction.

3. The method according to claim 1, wherein the key moments include: heel touching the ground, toes touching the ground, heel lifting off the ground, and/or toes lifting off the ground.

4. The method according to claim 1, further comprising a step of preprocessing the acceleration, angular velocity, and orientation values of the sole, said step of preprocessing including at least one processing selected from: frequency filtering, suppression of gravity on the acceleration values, suppression of gravity, suppression of noise and/or drift on the acceleration, angular velocity, and orientation values of the sole.

5. The method according to claim 4, wherein the preprocessing step is carried out in the electronic box integrated into the sole.

6. The method according to claim 1, further comprising a step of identifying the motion unit.

7. The method according to claim 1, wherein the step of identifying the activity associated with the motion unit includes calculating one or more global descriptive parameters from the acceleration, angular velocity, and/or magnetic field values, said global descriptive parameters including a kurtosis or skewness coefficient value.

8. The method according to claim 1, wherein the step of identifying the activity associated with the motion unit includes calculating one or more global descriptive parameters from the acceleration, angular velocity, and/or magnetic field values, said global descriptive parameters including one or more values of similarity coefficients with predetermined patterns.

9. The method according to claim 1, wherein the step of identifying the activity associated with the motion unit includes a probabilistic recognition step and/or a deterministic recognition step.

10. The method according to claim 1, wherein the step of identifying the at least two key moments is carried out in the electronic box integrated into the sole.

11. The method according to claim 1, wherein the step of determining the advanced biomechanical gait parameter value is carried out in the electronic box integrated into the sole.

12. The method according to claim 1, further comprising a step of calculating a combinatorial pattern of advanced biomechanical parameter values, said combinatorial pattern of advanced biomechanical parameter values corresponding to a combination of advanced biomechanical parameter values or a time-dependent behavior combination of advanced biomechanical parameters.

13. A system for determining an advanced biomechanical gait parameter value from data generated by one or more motion sensors of a sole, comprising:

at least one electronic box integrated into the sole, the electronic box including:

two sets of one or more motion sensors of the sole, where a first set can be associated with a first sole or shoe and a second set can be associated with a second sole or shoe, each set being configured to generate data including acceleration, angular velocity, and/or magnetic field values:

one or more analysis modules configured to determine an advanced biomechanical gait parameter value, said one or more analysis modules being configured to:

acquire the data generated by the one or more motion sensors;

calculate an orientation value of the sole, said orientation value of the sole being calculated with respect to a terrestrial reference frame from data including the acceleration, angular speed, and/or magnetic field values;

identify an activity associated with a motion unit, said identification of the activity including comparing activity reference values with values selected from: acceleration, angular speed, and/or orientation values of the sole, or global descriptive parameter values calculated from the acceleration, angular speed, and/or orientation values of the sole;

identify at least two key moments of the motion unit for which the activity has been identified, said step of identifying key moments including comparing motion parameter values with at least one predetermined threshold, said predetermined threshold being associated with the identified activity and said motion parameter values including acceleration, angular speed, and/or orientation values of the sole; and determine an advanced biomechanical gait parameter value, said determination including calculating a biomechanical gait parameter value for at least one of the identified key moments and from the acceleration, angular speed, and/or orientation values of the sole.

14. The system for determining an advanced biomechanical gait parameter value according to claim 13, wherein the pair of sets of one or more motion sensors of the sole corresponds to a pair of electronic boxes adapted to be integrated into a pair of soles.

15. The system for determining an advanced biomechanical gait parameter value according to claim 14, further comprising several processing modules configured to each perform part of the determination of the advanced biomechanical gait parameter value.

* * * * *